(12) United States Patent
Guillemont et al.

(10) Patent No.: US 9,758,497 B2
(45) Date of Patent: Sep. 12, 2017

(54) ANTIBACTERIAL COMPOUNDS

(71) Applicant: Janssen Sciences Ireland UC, Little Island, Co Cork (IE)

(72) Inventors: Jérôme Émile Georges Guillemont, Andé (FR); Magali Madeleine Simone Motte, Louviers (FR); Anil Koul, Edegem (BE); Nacer Lounis, Beerse (BE)

(73) Assignee: Janssen Sciences Ireland UC, Little Island (IE)

( * ) Notice: Subject to any disclaimer, the term of this patent is extended or adjusted under 35 U.S.C. 154(b) by 0 days.

(21) Appl. No.: 15/231,389

(22) Filed: Aug. 8, 2016

(65) Prior Publication Data

US 2016/0347728 A1 Dec. 1, 2016

Related U.S. Application Data

(63) Continuation of application No. 14/654,186, filed as application No. PCT/EP2013/077565 on Dec. 20, 2013, now Pat. No. 9,428,474.

(30) Foreign Application Priority Data

Dec. 21, 2012 (EP) .................................... 12199026

(51) Int. Cl.
*C07D 263/58* (2006.01)
*C07D 277/82* (2006.01)

(52) U.S. Cl.
CPC ......... *C07D 277/82* (2013.01); *C07D 263/58* (2013.01)

(58) Field of Classification Search
CPC ........................... C07D 277/82; C07D 263/58
See application file for complete search history.

(56) References Cited

U.S. PATENT DOCUMENTS

| 6,214,851 B1 | 4/2001 | Duncia |
| 9,428,474 B2 * | 8/2016 | Guillemont .......... A61K 31/423 |
| 2015/0344449 A1 | 12/2015 | Guillemont et al. |

FOREIGN PATENT DOCUMENTS

| DE | 2003841 | 1/1969 |
| WO | WO 00/56725 | 9/2000 |
| WO | WO 2004/011436 | 2/2004 |
| WO | WO 2004/105755 | 12/2004 |
| WO | WO 2005/023818 | 3/2005 |
| WO | WO 2005/037845 | 4/2005 |
| WO | WO 2007/140439 | 12/2007 |

OTHER PUBLICATIONS

European Search Report completed Feb. 27, 2013 for Application No. EP12199026.
International Search Report completed Jun. 23, 2014 for Application No. PCT/EP PCT/EP2013/077565.
Brown, J., et al., "The Structure-Activity Relationship of Urea Derivatives as Anti-Tuberculosis Agents", Bioorganic & Medicinal Chemistry, vol. 19, pp. 5585-5595 (2011).
Kolocouris, A., et al., "Improper Hydrogen Bonded Cyclohenane C—$H_{ax}$ Contacts: Theoretical predictions and Experimental Evidence from $^1$H NMR Spectroscopy of Suitable Axial Cyclohexane Models", Journal of Organic Chemistry, vol. 76, pp. 4432-4443 (2011).
Paget, C., et al., "Heterocyclic Substituted Ureas. II. Immunosuppressive and Antiviral Activity of Benzothiazole-and Benzoxazoleureas", Journal of Medicinal Chemistry, vol. 12(5), pp. 1016-1018 (1969).
Paget, C., et al., "Heterocyclic Substituted Ureas. I. Immunosuppression and Virus Inhibition by Benzimidazoleureas", Journal of Medicinal Chemistry, vol. 12(5), pp. 1010-1015 (1969).
Settimo, A., et al., Synthesis and Evaluation of Aminoadamantae Derivatives for In Vitro Anti-HIB and Antitumor Activities, II Farmaco, vol. 50, (5), pp. 321-326(1995).
Database Registry, Chemical Abstracts, XP002692931, Accession No. 1045924-81-9, Sep. 3, 2008.
Database Registry, Chemical Abstracts, XP002692932, Accession No. 892821-81-7, Jul. 16, 2006.
PubChem CI D 41327880—National Center for Biotechnology Information. PubChem Compound Database; CID=41327880, https://pubchem.ncbi.nlm.nih.gov/compound/41327880 (accessed Jan. 5, 2016), create date May 30, 2009.
Chemical Abstracts Registry No. 313403-16-6, indexed in the Registry file on STN CAS Online Jan. 10, 2001.
Chemical Abstracts Registry No. 295787-87-0, indexed in the Registry file on STN CAS Online Oct. 19, 2000.

\* cited by examiner

*Primary Examiner* — Laura L. Stockton

(57) ABSTRACT

The present invention relates to the following compounds for use in the treatment of a bacterial infection

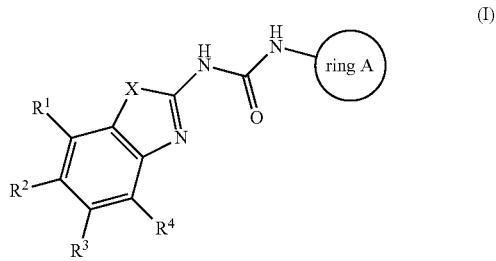

(I)

wherein the integers are as defined in the description. The invention also relates to compounds for use as medicaments, pharmaceutical compositions and some novel compounds.

2 Claims, No Drawings

ANTIBACTERIAL COMPOUNDS

This application is a continuation application of U.S. application Ser. No. 14/654,186 filed on Jun. 19, 2015, which is a 35 U.S.C. §371 nationalization of PCT application PCT/EP2013/077565 filed on Dec. 20, 2013, which claims priority to European patent application EP 12199026.1 filed Dec. 21, 2012.

The present invention relates to novel substituted benzazole derivatives, which are substituted with a urea moiety attached to a bridged cycloalkyl group. The invention also relates to such compounds for use as a pharmaceutical and further for the use in the treatment of bacterial diseases, including but not limited to diseases caused by pathogenic mycobacteria such as *Mycobacterium tuberculosis, M. bovis, M. leprae, M. avium* and *M. marinum*, or pathogenic Staphylococci or Streptococci.

BACKGROUND OF THE INVENTION

*Mycobacterium tuberculosis* is the causative agent of tuberculosis (TB), a serious and potentially fatal infection with a world-wide distribution. Estimates from the World Health Organization indicate that more than 8 million people contract TB each year, and 2 million people die from tuberculosis yearly. In the last decade, TB cases have grown 20% worldwide with the highest burden in the most impoverished communities. If these trends continue, TB incidence will increase by 41% in the next twenty years. Fifty years since the introduction of an effective chemotherapy, TB remains after AIDS, the leading infectious cause of adult mortality in the world. Complicating the TB epidemic is the rising tide of multi-drug-resistant strains, and the deadly symbiosis with HIV. People who are HIV-positive and infected with TB are 30 times more likely to develop active TB than people who are HIV-negative and TB is responsible for the death of one out of every three people with HIV/AIDS worldwide Existing approaches to treatment of tuberculosis all involve the combination of multiple agents. For example, the regimen recommended by the U.S. Public Health Service is a combination of isoniazid, rifampicin and pyrazinamide for two months, followed by isoniazid and rifampicin alone for a further four months. These drugs are continued for a further seven months in patients infected with HIV. For patients infected with multi-drug resistant strains of *M. tuberculosis*, agents such as ethambutol, streptomycin, kanamycin, amikacin, capreomycin, ethionamide, cycloserine, ciprofoxacin and ofloxacin are added to the combination therapies. There exists no single agent that is effective in the clinical treatment of tuberculosis, nor any combination of agents that offers the possibility of therapy of less than six months' duration.

There is a high medical need for new drugs that improve current treatment by enabling regimens that facilitate patient and provider compliance. Shorter regimens and those that require less supervision are the best way to achieve this. Most of the benefit from treatment comes in the first 2 months, during the intensive, or bactericidal, phase when four drugs are given together; the bacterial burden is greatly reduced, and patients become noninfectious. The 4- to 6-month continuation, or sterilizing, phase is required to eliminate persisting bacilli and to minimize the risk of relapse. A potent sterilizing drug that shortens treatment to 2 months or less would be extremely beneficial. Drugs that facilitate compliance by requiring less intensive supervision also are needed. Obviously, a compound that reduces both the total length of treatment and the frequency of drug administration would provide the greatest benefit.

Complicating the TB epidemic is the increasing incidence of multi-drug-resistant strains or MDR-TB. Up to four percent of all cases worldwide are considered MDR-TB—those resistant to the most effective drugs of the four-drug standard, isoniazid and rifampin. MDR-TB is lethal when untreated and cannot be adequately treated through the standard therapy, so treatment requires up to 2 years of "second-line" drugs. These drugs are often toxic, expensive and marginally effective. In the absence of an effective therapy, infectious MDR-TB patients continue to spread the disease, producing new infections with MDR-TB strains. There is a high medical need for a new drug with a new mechanism of action, which is likely to demonstrate activity against drug resistant, in particular MDR strains.

The term "drug resistant" as used hereinbefore or hereinafter is a term well understood by the person skilled in microbiology. A drug resistant *Mycobacterium* is a *Mycobacterium* which is no longer susceptible to at least one previously effective drug; which has developed the ability to withstand antibiotic attack by at least one previously effective drug. A drug resistant strain may relay that ability to withstand to its progeny. Said resistance may be due to random genetic mutations in the bacterial cell that alters its sensitivity to a single drug or to different drugs.

MDR tuberculosis is a specific form of drug resistant tuberculosis due to a bacterium resistant to at least isoniazid and rifampicin (with or without resistance to other drugs), which are at present the two most powerful anti-TB drugs. Thus, whenever used hereinbefore or hereinafter "drug resistant" includes multi drug resistant.

Another factor in the control of the TB epidemic is the problem of latent TB. In spite of decades of tuberculosis (TB) control programs, about 2 billion people are infected by *M. tuberculosis*, though asymptomatically. About 10% of these individuals are at risk of developing active TB during their lifespan. The global epidemic of TB is fuelled by infection of HIV patients with TB and rise of multi-drug resistant TB strains (MDR-TB). The reactivation of latent TB is a high risk factor for disease development and accounts for 32% deaths in HIV infected individuals. To control TB epidemic, the need is to discover new drugs that can kill dormant or latent bacilli. The dormant TB can get reactivated to cause disease by several factors like suppression of host immunity by use of immunosuppressive agents like antibodies against tumor necrosis factor α or interferon-γ. In case of HIV positive patients the only prophylactic treatment available for latent TB is two-three months regimens of rifampicin, pyrazinamide. The efficacy of the treatment regime is still not clear and furthermore the length of the treatments is an important constrain in resource-limited environments. Hence there is a drastic need to identify new drugs, which can act as chemoprophylatic agents for individuals harboring latent TB bacilli.

The tubercle bacilli enter healthy individuals by inhalation; they are phagocytosed by the alveolar macrophages of the lungs. This leads to potent immune response and formation of granulomas, which consist of macrophages infected with *M. tuberculosis* surrounded by T cells. After a period of 6-8 weeks the host immune response cause death of infected cells by necrosis and accumulation of caseous material with certain extracellular bacilli, surrounded by macrophages, epitheloid cells and layers of lymphoid tissue at the periphery. In case of healthy individuals, most of the mycobacteria are killed in these environments but a small proportion of bacilli still survive and are thought to exist in a non-replicating, hypometabolic state and are tolerant to killing by anti-TB drugs like isoniazid. These bacilli can remain in the altered physiological environments even for individual's lifetime without showing any clinical symptoms of disease. However, in 10% of the cases these latent bacilli may reactivate to cause disease. One of the hypothesis about development of these persistent bacteria is pathophysiological environment in human lesions namely, reduced oxygen tension, nutrient limitation, and acidic pH. These factors have been postulated to render these bacteria phenotypically tolerant to major anti-mycobacterial drugs.

In addition to the management of the TB epidemic, there is the emerging problem of resistance to first-line antibiotic agents. Some important examples include penicillin-resistant *Streptococcus pneumoniae*, vancomycin-resistant enterococci, methicillin-resistant *Staphylococcus aureus*, multi-resistant salmonellae.

The consequences of resistance to antibiotic agents are severe. Infections caused by resistant microbes fail to respond to treatment, resulting in prolonged illness and greater risk of death. Treatment failures also lead to longer periods of infectivity, which increase the numbers of infected people moving in the community and thus exposing the general population to the risk of contracting a resistant strain infection. Hospitals are a critical component of the antimicrobial resistance problem worldwide. The combination of highly susceptible patients, intensive and prolonged antimicrobial use, and cross-infection has resulted in infections with highly resistant bacterial pathogens.

Self-medication with antimicrobials is another major factor contributing to resistance. Self-medicated antimicrobials may be unnecessary, are often inadequately dosed, or may not contain adequate amounts of active drug.

Patient compliance with recommended treatment is another major problem. Patients forget to take medication, interrupt their treatment when they begin to feel better, or may be unable to afford a full course, thereby creating an ideal environment for microbes to adapt rather than be killed.

Because of the emerging resistance to multiple antibiotics, physicians are confronted with infections for which there is no effective therapy. The morbidity, mortality, and financial costs of such infections impose an increasing burden for health care systems worldwide.

Therefore, there is a high need for new compounds to treat bacterial infections, especially mycobacterial infections including drug resistant and latent mycobacterial infections, and also other bacterial infections especially those caused by resistant bacterial strains.

International patent application WO 2007/140439 discloses various compounds that may be useful as cannabinoid receptor ligands. However, this document only discloses fused bicycles in which the "azole" moiety is non-aromatic.

International patent application WO 2005/037845 discloses various benzothiazoles, which are substituted with a urea attached to an adamantly group. However, this document only discloses compounds as ubiquitin ligase inhibitors.

International patent application WO 2004/105755 discloses various benzothiazoles, but such compounds are only disclosed as being useful for the treatment of diseases related to the adenosine A2A receptor. International patent application WO 2000/056725 discloses various benzothiazoles, but such compounds are only disclosed for use as anti-inflammatory and radiosensitizing agents. International patent application WO 99/24035 discloses benzothiazoles, but such compounds are only disclosed as protein tyrosine kinase inhibitors. German patent application DE 1970-2003841 (and equivalents) discloses certain benzimidazoles and tricycles, however, such compounds are only disclosed in the context of antivirals and immunization reaction-suppression.

Journal article "Farmaco (1995), 50(5), 321-6" by Da Settimo et al and Journal of Medicinal Chemistry (1969), 12(5), 1010-15 and 1016-18 by Paget et al all disclose various benimidazoles, however, such compounds are only disclosed in the context of in vitro studies for anti-HIV and antitumor activities (or generally for immunosuppression and virus inhibition).

International patent application WO 2005/023818 discloses the preparation of various compounds as pharmaceutically active agents. However, this document does not disclose any benzazoles.

The journal article *Bioorganic & Medicinal Chemistry* 19 (2011) 5585-5595 by Brown et al discloses the structure-activity relationship of urea derivatives. However, this document does not disclose or relate to any fused bicyclic heteroaromatic structures.

Several other compounds have apparently been disclosed on the CAS Registry database, which have no use ascribed to them. For example, compounds with Registry numbers 1045924-81-9 and 892821-81-7 are such compounds that have no use ascribed.

The purpose of the present invention is to provide compounds for use in inhibiting bacterial growth especially of Streptococci, Staphylococci or mycobacteria and therefore useful for the treatment of bacterial diseases, particularly those diseases caused by pathogenic bacteria such as *Streptococcus pneumonia, Staphylococcus aureus* or *Mycobacterium tuberculosis* (including the latent disease and including drug resistant *M. tuberculosis* strains), *M. bovis, M. leprae, M. avium* and *M. marinum*. Such compounds may also be novel.

SUMMARY OF THE INVENTION

There is now provided a compound of formula (I) for use in the treatment of a bacterial infection (e.g. a mycobacterial infection), wherein the compound of formula (I) represents:

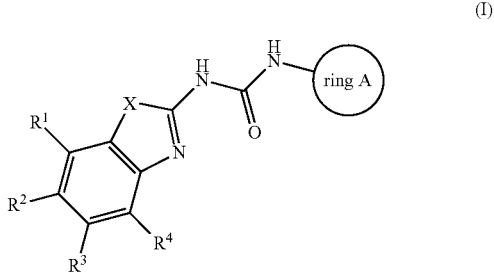

wherein $R^1$, $R^2$, $R^3$ and $R^4$ each independently represent hydrogen, halo, —CN, $R^{t1}$, —O—$R^{t2}$, —C(O)N($R^{t3}$)($R^{t4}$), —SO$_2R^{t5}$, —N(H)SO$_2R^{t6}$, —N($R^{t7}$)($R^{t8}$) or an aryl or heterocyclic group (which latter two groups are themselves optionally substituted by one or more substituents selected from halo and $C_{1-6}$ alkyl);

$R^{t1}$, $R^{t2}$, $R^{t3}$, $R^{t4}$, $R^{t5}$, $R^{t6}$, $R^{t7}$ and $R^{t8}$ independently represent hydrogen or $C_{1-6}$ alkyl optionally substituted by one or more halo atoms, or $R^{t3}$ and $R^{t4}$ and/or $R^{t7}$ and $R^{t8}$ may be linked together with the nitrogen atom to which they are attached to form a 3- to 7-membered ring, optionally containing one to three (e.g. one) further heteroatom(s) and optionally contain one to three double bonds;

$Z^x$ represents O or S;
X represents S or O;
ring A represents either:

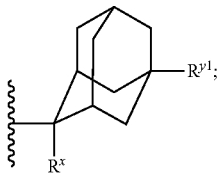

(i)

or

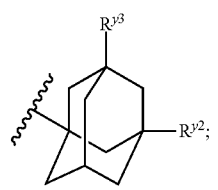

(ii)

$R^x$ represents hydrogen or $C_{1-6}$ alkyl optionally substituted by one or more substituents selected from fluoro, —CN, —$OR^{x1}$, —$C(O)R^{x2}$ and —$C(O)NR^{x3}$;

$R^{x1}$, $R^{x2}$ and $R^{x3}$ independently represent hydrogen or $C_{1-6}$ alkyl;

$R^{y1}$, $R^{y2}$ and $R^{y3}$ independently represent hydrogen, halo (e.g. fluoro), $C_{1-6}$ alkyl, —$OR^{y4}$, —$C(O)$—$R^{y5}$ or —$CH_2$—$OR^{y6}$;

$R^{y4}$, $R^{y5}$ and $R^{y6}$ independently represent hydrogen or $C_{1-6}$ alkyl;

or a pharmaceutically acceptable salt (e.g. acid addition salt) thereof.

The above-mentioned compounds of formula (I) (or salts thereof) may be referred to herein as "compounds of the invention". Such compounds are indicated as being useful in the treatment of a bacterial infection. However, some compounds mentioned above may also be useful as medicaments, and some compounds may be novel.

Hence, in a further embodiment of the invention, there is a compound of formula I, for use as a pharmaceutical, as defined herein, but in which:

$R^1$, $R^2$, $R^3$ and $R^4$ each independently represent hydrogen, fluoro or $C_{1-6}$ alkyl (optionally substituted by one or more halo substituents). Such compounds may also be contained/comprised in pharmaceutical formulations/compositions.

In a further embodiment of the invention, there is provided novel compounds per se. In this respect, there is provided a compound of formula I, as defined herein, but in which:

$R^1$, $R^2$, $R^3$ and $R^4$ each independently represent hydrogen, fluoro or $C_{1-6}$ alkyl optionally substituted by one or more halo substituents (but which alkyl group is preferably substituted with one or more halo atoms);

for instance, in which:
one or two of $R^1$ to $R^4$ represents fluoro, and the remaining represent hydrogen;
one of $R^1$ to $R^4$ represents —$CF_3$, and the remaining represent hydrogen.

Insofar as the embodiment of the invention in which novel compounds per se are concerned, the following compounds are preferably excluded from the scope, compounds of formula I in which X represents S, $Z^x$ represents O, $R^1$ and $R^4$ represent H, $R^2$ represents —$CH_3$, ring A represents ring (ii) in which $R^{y2}$ and $R^{y3}$ both represent hydrogen, and $R^3$ represents hydrogen or —$CH_3$.

The above mentioned embodiments of the invention (for use as a pharmaceutical and the novel per se compounds) may be combined with other preferred features of the invention, for instance those described hereinafter.

Pharmaceutically-acceptable salts include acid addition salts and base addition salts. Such salts may be formed by conventional means, for example by reaction of a free acid or a free base form of a compound of formula I with one or more equivalents of an appropriate acid or base, optionally in a solvent, or in a medium in which the salt is insoluble, followed by removal of said solvent, or said medium, using standard techniques (e.g. in vacuo, by freeze-drying or by filtration). Salts may also be prepared by exchanging a counter-ion of a compound of the invention in the form of a salt with another counter-ion, for example using a suitable ion exchange resin.

The pharmaceutically acceptable acid addition salts as mentioned hereinabove are meant to comprise the therapeutically active non-toxic acid addition salt forms that the compounds of formula (I) are able to form. These pharmaceutically acceptable acid addition salts can conveniently be obtained by treating the base form with such appropriate acid. Appropriate acids comprise, for example, inorganic acids such as hydrohalic acids, e.g. hydrochloric or hydrobromic acid, sulfuric, nitric, phosphoric and the like acids; or organic acids such as, for example, acetic, propanoic, hydroxyacetic, lactic, pyruvic, oxalic (i.e. ethanedioic), malonic, succinic (i.e. butanedioic acid), maleic, fumaric, malic, tartaric, citric, methanesulfonic, ethanesulfonic, benzenesulfonic, p-toluenesulfonic, cyclamic, salicylic, p-aminosalicylic, pamoic and the like acids.

For the purposes of this invention solvates, prodrugs, N-oxides and stereoisomers of compounds of the invention are also included within the scope of the invention.

The term "prodrug" of a relevant compound of the invention includes any compound that, following oral or parenteral administration, is metabolised in vivo to form that compound in an experimentally-detectable amount, and within a predetermined time (e.g. within a dosing interval of between 6 and 24 hours (i.e. once to four times daily)).

For the avoidance of doubt, the term "parenteral" administration includes all forms of administration other than oral administration.

Prodrugs of compounds of the invention may be prepared by modifying functional groups present on the compound in such a way that the modifications are cleaved, in vivo when such prodrug is administered to a mammalian subject. The modifications typically are achieved by synthesising the parent compound with a prodrug substituent. Prodrugs include compounds of the invention wherein a hydroxyl, amino, sulfhydryl, carboxy or carbonyl group in a compound of the invention is bonded to any group that may be cleaved in vivo to regenerate the free hydroxyl, amino, sulfhydryl, carboxy or carbonyl group, respectively.

Examples of prodrugs include, but are not limited to, esters and carbamates of hydroxy functional groups, esters groups of carboxyl functional groups, N-acyl derivatives and N-Mannich bases. General information on prodrugs may be found e.g. in Bundegaard, H. "Design of Prodrugs" p. 1-92, Elesevier, New York-Oxford (1985).

Compounds of the invention may contain double bonds and may thus exist as E (entgegen) and Z (zusammen) geometric isomers about each individual double bond. Positional isomers may also be embraced by the compounds of the invention. All such isomers (e.g. if a compound of the invention incorporates a double bond or a fused ring, the cis- and trans-forms, are embraced) and mixtures thereof are included within the scope of the invention (e.g. single positional isomers and mixtures of positional isomers may be included within the scope of the invention).

Compounds of the invention may also exhibit tautomerism. All tautomeric forms (or tautomers) and mixtures thereof are included within the scope of the invention. The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerisations. Valence tautomers include interconversions by reorganisation of some of the bonding electrons.

Compounds of the invention may also contain one or more asymmetric carbon atoms and may therefore exhibit optical and/or diastereoisomerism. Diastereoisomers may be separated using conventional techniques, e.g. chromatography or fractional crystallisation. The various stereoisomers may be isolated by separation of a racemic or other mixture of the compounds using conventional, e.g. fractional crystallisation or HPLC, techniques. Alternatively the desired optical isomers may be made by reaction of the appropriate optically active starting materials under conditions which will not cause racemisation or epimerisation (i.e. a 'chiral pool' method), by reaction of the appropriate starting material with a 'chiral auxiliary' which can subsequently be removed at a suitable stage, by derivatisation (i.e. a resolution, including a dynamic resolution), for example with a homochiral acid followed by separation of the diastereomeric derivatives by conventional means such as chromatography, or by reaction with an appropriate chiral reagent or chiral catalyst all under conditions known to the skilled person.

All stereoisomers (including but not limited to diastereoisomers, enantiomers and atropisomers) and mixtures thereof (e.g. racemic mixtures) are included within the scope of the invention.

In the structures shown herein, where the stereochemistry of any particular chiral atom is not specified, then all stereoisomers are contemplated and included as the compounds of the invention. Where stereochemistry is specified by a solid wedge or dashed line representing a particular configuration, then that stereoisomer is so specified and defined.

The compounds of the present invention may exist in unsolvated as well as solvated forms with pharmaceutically acceptable solvents such as water, ethanol, and the like, and it is intended that the invention embrace both solvated and unsolvated forms.

The present invention also embraces isotopically-labeled compounds of the present invention which are identical to those recited herein, but for the fact that one or more atoms are replaced by an atom having an atomic mass or mass number different from the atomic mass or mass number usually found in nature (or the most abundant one found in nature). All isotopes of any particular atom or element as specified herein are contemplated within the scope of the compounds of the invention. Exemplary isotopes that can be incorporated into compounds of the invention include isotopes of hydrogen, carbon, nitrogen, oxygen, phosphorus, sulfur, fluorine, chlorine and iodine, such as $^2$H, $^3$H, $^{11}$C, $^{13}$C, $^{14}$C, $^{13}$N, $^{15}$O, $^{17}$O, $^{18}$O, $^{32}$P, $^{33}$P, $^{35}$S, $^{18}$F, $^{36}$Cl, $^{123}$I, and $^{125}$I. Certain isotopically-labeled compounds of the present invention (e.g., those labeled with $^3$H and $^{14}$C) are useful in compound and for substrate tissue distribution assays. Tritiated (3H) and carbon-14 ($^{14}$C) isotopes are useful for their ease of preparation and detectability. Further, substitution with heavier isotopes such as deuterium (i.e., $^2$H may afford certain therapeutic advantages resulting from greater metabolic stability (e.g., increased in vivo half-life or reduced dosage requirements) and hence may be preferred in some circumstances. Positron emitting isotopes such as $^{15}$O, $^{13}$N, $^{11}$C and $^{18}$F are useful for positron emission tomography (PET) studies to examine substrate receptor occupancy. Isotopically labeled compounds of the present invention can generally be prepared by following procedures analogous to those disclosed in the Scheme 1 and/or in the Examples herein below, by substituting an isotopically labeled reagent for a non-isotopically labeled reagent.

Unless otherwise specified, $C_{1-q}$ alkyl groups (where q is the upper limit of the range) defined herein may be straight-chain or, when there is a sufficient number (i.e. a minimum of two or three, as appropriate) of carbon atoms, be branched-chain, and/or cyclic (so forming a $C_{3-q}$-cycloalkyl group). Such cycloalkyl groups may be monocyclic or bicyclic and may further be bridged. Further, when there is a sufficient number (i.e. a minimum of four) of carbon atoms, such groups may also be part cyclic. Such alkyl groups may also be saturated or, when there is a sufficient number (i.e. a minimum of two) of carbon atoms, be unsaturated (forming, for example, a $C_{2-q}$ alkenyl or a $C_{2-q}$ alkynyl group).

$C_{3-q}$ cycloalkyl groups (where q is the upper limit of the range) that may be specifically mentioned may be monocyclic or bicyclic alkyl groups, which cycloalkyl groups may further be bridged (so forming, for example, fused ring systems such as three fused cycloalkyl groups). Such cycloalkyl groups may be saturated or unsaturated containing one or more double bonds (forming for example a cycloalkenyl group). Substituents may be attached at any point on the cycloalkyl group. Further, where there is a sufficient number (i.e. a minimum of four) such cycloalkyl groups may also be part cyclic.

The term "halo", when used herein, preferably includes fluoro, chloro, bromo and iodo.

Heterocyclic groups when referred to herein may include aromatic or non-aromatic heterocyclic groups, and hence encompass heterocycloalkyl and hetereoaryl.

Heterocycloalkyl groups that may be mentioned include non-aromatic monocyclic and bicyclic heterocycloalkyl groups in which at least one (e.g. one to four) of the atoms in the ring system is other than carbon (i.e. a heteroatom), and in which the total number of atoms in the ring system is between 3 and 20 (e.g. between three and ten, e.g between 3 and 8, such as 5- to 8-). Such heterocycloalkyl groups may also be bridged. Further, such heterocycloalkyl groups may be saturated or unsaturated containing one or more double and/or triple bonds, forming for example a $C_{2-q}$ heterocycloalkenyl (where q is the upper limit of the range) group. $C_{2-q}$ heterocycloalkyl groups that may be mentioned include 7-azabicyclo[2.2.1]heptanyl, 6-azabicyclo[3.1.1]heptanyl, 6-azabicyclo[3.2.1]-octanyl, 8-azabicyclo-[3.2.1]octanyl, aziridinyl, azetidinyl, dihydropyranyl, dihydropyridyl, dihydropyrrolyl (including 2,5-dihydropyrrolyl), dioxolanyl (including 1,3-dioxolanyl), dioxanyl (including 1,3-dioxanyl and 1,4-dioxanyl), dithianyl (including 1,4-dithianyl), dithiolanyl (including 1,3-dithiolanyl), imidazolidinyl, imidazolinyl, morpholinyl, 7-oxabicyclo[2.2.1]heptanyl, 6-oxabicyclo-[3.2.1]octanyl, oxetanyl, oxiranyl, piperazinyl, piperidinyl, non-aromatic pyranyl, pyrazolidinyl, pyrrolidinonyl, pyrrolidinyl, pyrrolinyl, quinuclidinyl, sulfolanyl, 3-sulfolenyl, tetrahydropyranyl, tetrahydrofuranyl, tetrahydropyridyl (such as 1,2,3,4-tetrahydropyridyl and 1,2,3,6-tetrahydropyridyl), thietanyl, thiiranyl, thiolanyl, thiomorpholinyl, trithianyl (including 1,3,5-trithianyl), tropanyl and the like. Substituents on heterocycloalkyl groups may, where appropriate, be located on any atom in the ring system including a heteroatom. The point of attachment of heterocycloalkyl groups may be via any atom in the ring system including (where appropriate) a heteroatom (such as a nitrogen atom), or an atom on any fused carbocyclic ring that may be present as part of the ring system. Heterocycloalkyl groups may also be in the N- or S-oxidised form. Heterocycloalkyl mentioned herein may be stated to be specifically monocyclic or bicyclic.

Aryl groups that may be mentioned include $C_{6-20}$, such as $C_{6-12}$ (e.g. $C_{6-10}$) aryl groups. Such groups may be monocyclic, bicyclic or tricyclic and have between 6 and 12 (e.g. 6 and 10) ring carbon atoms, in which at least one ring is aromatic. $C_{6-10}$ aryl groups include phenyl, naphthyl and the like, such as 1,2,3,4-tetrahydronaphthyl. The point of attachment of aryl groups may be via any atom of the ring system. For example, when the aryl group is polycyclic the point of attachment may be via atom including an atom of a non-aromatic ring. However, when aryl groups are polycyclic (e.g. bicyclic or tricyclic), they are preferably linked to the rest of the molecule via an aromatic ring. Most preferred aryl groups that may be mentioned herein are "phenyl".

Unless otherwise specified, the term "heteroaryl" when used herein refers to an aromatic group containing one or more heteroatom(s) (e.g. one to four heteroatoms) preferably selected from N, O and S. Heteroaryl groups include those which have between 5 and 20 members (e.g. between 5 and 10) and may be monocyclic, bicyclic or tricyclic, provided that at least one of the rings is aromatic (so forming, for example, a mono-, bi-, or tricyclic heteroaromatic group). When the heteroaryl group is polycyclic the point of attachment may be via any atom including an atom of a non-aromatic ring.

However, when heteroaryl groups are polycyclic (e.g. bicyclic or tricyclic), they are preferably linked to the rest of the molecule via an aromatic ring. Heteroaryl groups that may be mentioned include 3,4-dihydro-1H-isoquinolinyl, 1,3-dihydroisoindolyl, 1,3-dihydroisoindolyl (e.g. 3,4-dihydro-1H-isoquinolin-2-yl, 1,3-dihydroisoindol-2-yl, 1,3-dihydroisoindol-2-yl; i.e. heteroaryl groups that are linked via a non-aromatic ring), or, preferably, acridinyl, benzimidazolyl, benzodioxanyl, benzodioxepinyl, benzo-dioxolyl (including 1,3-benzodioxolyl), benzofuranyl, benzofurazanyl, benzothiadiazolyl (including 2,1,3-benzothiadiazolyl), benzothiazolyl, benzoxadiazolyl (including 2,1,3-benzoxadiazolyl), benzoxazinyl (including 3,4-dihydro-2H-1,4-benzoxazinyl), benzoxazolyl, benzomorpholinyl, benzoselenadiazolyl (including 2,1,3-benzoselenadiazolyl), benzothienyl, carbazolyl, chromanyl, cinnolinyl, furanyl, imidazolyl, imidazo[1,2-α]pyridyl, indazolyl, indolinyl, indolyl, isobenzofuranyl, isochromanyl, isoindolinyl, isoindolyl, isoquinolinyl, isothiazolyl, isothiochromanyl, isoxazolyl, naphthyridinyl (including 1,6-naphthyridinyl or, preferably, 1,5-naphthyridinyl and 1,8-naphthyridinyl), oxadiazolyl (including 1,2,3-oxadiazolyl, 1,2,4-oxadiazolyl and 1,3,4-oxadiazolyl), oxazolyl, phenazinyl, phenothiazinyl, phthalazinyl, pteridinyl, purinyl, pyranyl, pyrazinyl, pyrazolyl, pyridazinyl, pyridyl, pyrimidinyl, pyrrolyl, quinazolinyl, quinolinyl, quinolizinyl, quinoxalinyl, tetrahydroisoquinolinyl (including 1,2,3,4-tetrahydroisoquinolinyl and 5,6,7,8-tetra-hydroisoquinolinyl), tetrahydroquinolinyl (including 1,2,3,4-tetrahydroquinolinyl and 5,6,7,8-tetrahydroquinolinyl), tetrazolyl, thiadiazolyl (including 1,2,3-thiadiazolyl, 1,2,4-thiadiazolyl and 1,3,4-thiadiazolyl), thiazolyl, thiochromanyl, thiophenetyl, thienyl, triazolyl (including 1,2,3-triazolyl, 1,2,4-triazolyl and 1,3,4-triazolyl) and the like. Substituents on heteroaryl groups may, where appropriate, be located on any atom in the ring system including a heteroatom. The point of attachment of heteroaryl groups may be via any atom in the ring system including (where appropriate) a heteroatom (such as a nitrogen atom), or an atom on any fused carbocyclic ring that may be present as part of the ring system. Heteroaryl groups may also be in the N- or S-oxidised form. Heteroaryl groups mentioned herein may be stated to be specifically monocyclic or bicyclic. When heteroaryl groups are polycyclic in which there is a non-aromatic ring present, then that non-aromatic ring may be substituted by one or more =O group. Most preferred heteroaryl groups that may be mentioned herein are 5- or 6-membered aromatic groups containing 1, 2 or 3 heteroatoms (e.g. preferably selected from nitrogen, oxygen and sulfur).

It may be specifically stated that the heteroaryl group is monocyclic or bicyclic. In the case where it is specified that the heteroaryl is bicyclic, then it may consist of a five-, six- or seven-membered monocyclic ring (e.g. a monocyclic heteroaryl ring) fused with another five-, six- or seven-membered ring (e.g. a monocyclic aryl or heteroaryl ring).

Heteroatoms that may be mentioned include phosphorus, silicon, boron and, preferably, oxygen, nitrogen and sulfur.

For the avoidance of doubt, where it is stated herein that a group may be substituted by one or more substituents (e.g. selected from $C_{1-6}$ alkyl), then those substituents (e.g. alkyl groups) are independent of one another. That is, such groups may be substituted with the same substituent (e.g. same alkyl substituent) or different (e.g. alkyl) substituents.

All individual features (e.g. preferred features) mentioned herein may be taken in isolation or in combination with any other feature (including preferred feature) mentioned herein (hence, preferred features may be taken in conjunction with other preferred features, or independently of them).

The skilled person will appreciate that compounds of the invention that are the subject of this invention include those that are stable. That is, compounds of the invention include those that are sufficiently robust to survive isolation from e.g. a reaction mixture to a useful degree of purity.

Compounds of the invention (per se or for any use mentioned herein) that may be mentioned include those in which:

$R^2$ preferably does not represent —O—$R'^2$;

$R^2$ preferably represents hydrogen, halo, —CN, $R'^1$, —C(O)N($R'^3$)($R'^4$), —SO$_2$$R'^5$, —N(H)SO$_2$$R'^6$, —N($R'^7$)($R'^8$) or an aryl or heterocyclic group (which latter two groups are themselves optionally substituted by one or more substituents selected from halo and $C_{1-6}$ alkyl);

none of $R^1$, $R^2$, $R^3$ and $R^4$ represent —O—$R'^2$; and/or $R^1$, $R^2$, $R^3$ and $R^4$ preferably each independently represent hydrogen, halo, —CN, $R'^1$, —C(O)N($R'^3$)($R'^4$)SO$_2$$R'^5$, —N(H)SO$_2$$R'^6$, —N($R'^7$)($R'^8$) or an aryl or heterocyclic group (which latter two groups are themselves optionally substituted by one or more substituents selected from halo and $C_{1-6}$ alkyl).

Preferred compounds of the invention include those in which:

when $R^1$, $R^2$, $R^3$ or $R^4$ represent aryl, then that aryl group is preferably naphthyl or, especially phenyl (which groups are preferably unsubstituted);

when $R^1$, $R^2$, $R^3$ or $R^4$ represent a heterocyclic group, then it is preferably a 5- or 6-membered heteroaryl group or a 3- to 6-membered heterocycloalkyl group (e.g. in which the heteroaryl or heterocycloalkyl group contain one or two heteroatoms, preferably selected from nitrogen, oxygen and sulfur, so forming e.g. furanyl, imidazolyl, and the like, and/or piperidinyl, piperazinyl, morpholinyl, azetidinyl, and the like);

when $R^{t3}$ and $R^{t4}$ and/or $R^{t7}$ and $R^{t8}$ are linked together they preferably form a 5- or 6-membered ring, optionally containing one further heteroatom (e.g. sulfur or preferably oxygen or nitrogen) and which are preferably saturated (so forming e.g. piperidinyl, morpholinyl, piperazinyl, pyrrolidinyl, and the like).

Preferred compounds of the invention include those in which:

$R^{y3}$ represents hydrogen;

$R^1$, $R^2$, $R^3$ and $R^4$ each independently represent hydrogen, halo, $C_{1-6}$ alkyl (optionally substituted by one or more halo substituents) or —$OC_{1-6}$ alkyl (wherein the alkyl moiety is optionally substituted by one or more halo substituents);

$R^{t1}$, $R^{t2}$, $R^{t3}$, $R^{t4}$, $R^{t5}$, $R^{t6}$, $R^{t7}$ and $R^{t8}$ independently represent hydrogen or $C_{1-6}$ (e.g. $C_{1-3}$) alkyl.

In an embodiment of the invention, ring A represents:

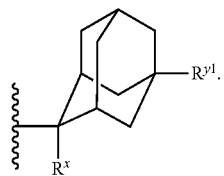

(i)

In another embodiment of the invention (which may be particularly preferred), ring A represents:

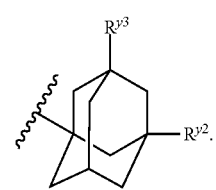

(ii)

Other preferred compounds of the invention include those in which:

$R^{y1}$ represents fluoro, chloro, $C_{1-6}$ alkyl, —OH, —C(O)$R^{y5}$ or —$CH_2$—$OR^{y6}$; and $R^{y2}$ represents —OH, $C_{1-6}$ alkyl (e.g. methyl), —C(O)$R^{y5}$ or —$CH_2$—$OR^{y6}$).

Compounds of the invention that are preferred include those in which:

$R^1$, $R^2$, $R^3$ and $R^4$ each independently represent hydrogen, halo, —C(O)(N$R^{t3}$)($R^{t4}$), $C_{1-6}$ alkyl (optionally substituted by one or more halo substituents), for instance, hydrogen, halo, —$CF_3$ or —$CH_3$;

preferably there is at least one $R^1$, $R^2$, $R^3$ or $R^4$ (e.g. $R^2$) substituent present and preferably one (e.g. at the $R^2$ or $R^3$ position) or two substituents (e.g. $R^2$ and $R^3$ or $R^2$ and $R^4$);

$Z^x$ represents O;

X represents O or S;

$R^{t3}$ and $R^{t4}$ independently represent hydrogen or preferably $C_{1-6}$ (e.g. $C_{1-3}$) alkyl (e.g. methyl);

$R^x$ represents hydrogen or $C_{1-6}$ alkyl;

$R^{x1}$ and $R^{x2}$ independently represent hydrogen or methyl;

$R^{y1}$ and $R^{y2}$ independently represent hydrogen, halo (e.g. fluoro) or $C_{1-6}$ alkyl;

$R^{y4}$, $R^{y5}$ and $R^{y6}$ independently represent hydrogen or methyl.

Further preferred compounds of the invention include those in which:

$R^1$, $R^2$, $R^3$ and $R^4$ each independently represent hydrogen, halo (e.g. fluoro or chloro), $C_{1-2}$ alkyl (optionally substituted by one or more fluoro atoms; so forming e.g. $CH_3$ or $CF_3$) or —C(O)N($C_{1-2}$ alkyl)$_2$ (e.g. —C(O)N($CH_3$)$_2$);

at least two of $R^1$, $R^2$, $R^3$ and $R^4$ represent hydrogen, and the others may represent hydrogen or a substituent as defined herein (e.g. —C(O)N($CH_3$)$_2$, —$CH_3$ or preferably halo and/or —$CF_3$).

Yet further preferred compounds of the invention include those in which:

$R^1$, $R^2$, $R^3$ and $R^4$ each independently represent hydrogen, halo (e.g. fluoro or chloro);

X represents O;

$R^x$ represents hydrogen;

$R^{x1}$ and $R^{x2}$ independently represent hydrogen;

$R^{y1}$ and $R^{y2}$ independently represent hydrogen;

$R^{y3}$, $R^{y4}$ and $R^{y5}$ independently represent hydrogen.

PHARMACOLOGY

The compounds according to the invention have surprisingly been shown to be suitable for the treatment of a bacterial infection including a mycobacterial infection, particularly those diseases caused by pathogenic mycobacteria such as *Mycobacterium tuberculosis* (including the latent and drug resistant form thereof), *M. bovis, M. leprae, M. avium, M. leprae* and *M. marinum*. The present invention thus also relates to compounds of the invention as defined hereinabove, the pharmaceutically acceptable salts thereof, the solvates thereof or the N-oxide forms thereof, for use as a medicine, in particular for use as a medicine for the treatment of a bacterial infection including a mycobacterial infection.

Further, the present invention also relates to the use of a compound of the invention, the pharmaceutically acceptable salts thereof, the solvates thereof or the N-oxide forms thereof, as well as any of the pharmaceutical compositions thereof as described hereinafter for the manufacture of a medicament for the treatment of a bacterial infection including a mycobacterial infection.

Accordingly, in another aspect, the invention provides a method of treating a patient suffering from, or at risk of, a bacterial infection, including a mycobacterial infection, which comprises administering to the patient a therapeutically effective amount of a compound or pharmaceutical composition according to the invention.

In addition to their activity against mycobacteria, the compounds according to the invention are also active against other bacteria. In general, bacterial pathogens may be classified as either gram-positive or gram-negative pathogens. Antibiotic compounds with activity against both gram-positive and gram-negative pathogens are generally regarded as having a broad spectrum of activity. The compounds of the present invention are regarded as active against gram-positive and/or gram-negative bacterial pathogens, in particular against gram-positive bacterial pathogens. In particular, the present compounds are active against at least one gram-positive bacterium, preferably against several gram-positive bacteria, more preferably against one or more gram-positive bacteria and/or one or more gram-negative bacteria.

The present compounds have bactericidal or bacteriostatic activity.

Examples of gram-positive and gram-negative aerobic and anaerobic bacteria, include Staphylococci, for example *S. aureus*; Enterococci, for example *E. faecalis*; Streptococci, for example *S. pneumoniae, S. mutans, S. pyogens*; Bacilli, for example *Bacillus subtilis; Listeria*, for example *Listeria monocytogenes; Haemophilus*, for example *H. influenza; Moraxella*, for example *M. catarrhalis; Pseudomonas*, for example *Pseudomonas aeruginosa*; and *Escherichia*, for example *E. coli*.

Gram-positive pathogens, for example Staphylococci, Enterococci and Streptococci are particularly important because of the development of resistant strains which are both difficult to treat and difficult to eradicate from for example a hospital environment once established. Examples of such strains are methicillin resistant *Staphylococcus aureus* (MRSA), methicillin resistant coagulase negative staphylococci (MRCNS), penicillin resistant *Streptococcus pneumoniae* and multiple resistant *Enterococcus faecium*.

The compounds of the present invention also show activity against resistant bacterial strains.

The compounds of the present invention are especially active against *Streptococcus pneumoniae* and *Staphylococcus aureus*, including resistant *Staphylococcus aureus* such as for example methicillin resistant *Staphylococcus aureus* (MRSA).

Therefore, the present invention also relates to the use of a compound of the invention, the pharmaceutically acceptable salts thereof, the solvates thereof or the N-oxide forms thereof, as well as any of the pharmaceutical compositions thereof as described hereinafter for the manufacture of a medicament for the treatment of a bacterial infection including an infection caused by Staphylococci and/or Streptococci.

Accordingly, in another aspect, the invention provides a method of treating a patient suffering from, or at risk of, a bacterial infection, including an infection caused by Staphylococci and/or Streptococci, which comprises administering to the patient a therapeutically effective amount of a compound or pharmaceutical composition according to the invention.

Without being bound to any theory, it is taught that the activity of the present compounds lies in inhibition of the F1F0 ATP synthase, in particular the inhibition of the F0 complex of the F1F0 ATP synthase, more in particular the inhibition of subunit c of the F0 complex of the F1F0 ATP synthase, leading to killing of the bacteria by depletion of the cellular ATP levels of the bacteria. Therefore, in particular, the compounds of the present invention are active on those bacteria of which the viability depends on proper functioning of F1F0 ATP synthase.

Bacterial infections which may be treated by the present compounds include, for example, central nervous system infections, external ear infections, infections of the middle ear, such as acute otitis media, infections of the cranial sinuses, eye infections, infections of the oral cavity, such as infections of the teeth, gums and mucosa, upper respiratory tract infections, lower respiratory tract infections, genitourinary infections, gastrointestinal infections, gynaecological infections, septicemia, bone and joint infections, skin and skin structure infections, bacterial endocarditis, burns, antibacterial prophylaxis of surgery, and antibacterial prophylaxis in immunosuppressed patients, such as patients receiving cancer chemotherapy, or organ transplant patients.

Whenever used hereinbefore or hereinafter, that the compounds can treat a bacterial infection it is meant that the compounds can treat an infection with one or more bacterial strains.

The invention also relates to a composition comprising a pharmaceutically acceptable carrier and, as active ingredient, a therapeutically effective amount of a compound according to the invention. The compounds according to the invention may be formulated into various pharmaceutical forms for administration purposes. As appropriate compositions there may be cited all compositions usually employed for systemically administering drugs. To prepare the pharmaceutical compositions of this invention, an effective amount of the particular compound, optionally in addition salt form, as the active ingredient is combined in intimate admixture with a pharmaceutically acceptable carrier, which carrier may take a wide variety of forms depending on the form of preparation desired for administration. These pharmaceutical compositions are desirable in unitary dosage form suitable, in particular, for administration orally or by parenteral injection. For example, in preparing the compositions in oral dosage form, any of the usual pharmaceutical media may be employed such as, for example, water, glycols, oils, alcohols and the like in the case of oral liquid preparations such as suspensions, syrups, elixirs, emulsions and solutions; or solid carriers such as starches, sugars, kaolin, diluents, lubricants, binders, disintegrating agents and the like in the case of powders, pills, capsules and tablets. Because of their ease in administration, tablets and capsules represent the most advantageous oral dosage unit forms in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. Also included are solid form preparations which are intended to be converted, shortly before use, to liquid form preparations.

Depending on the mode of administration, the pharmaceutical composition will preferably comprise from 0.05 to 99% by weight, more preferably from 0.1 to 70% by weight, even more preferably from 0.1 to 50% by weight of the active ingredient(s), and, from 1 to 99.95% by weight, more preferably from 30 to 99.9% by weight, even more preferably from 50 to 99.9% by weight of a pharmaceutically acceptable carrier, all percentages being based on the total weight of the composition.

The pharmaceutical composition may additionally contain various other ingredients known in the art, for example, a lubricant, stabilising agent, buffering agent, emulsifying agent, viscosity-regulating agent, surfactant, preservative, flavouring or colorant.

It is especially advantageous to formulate the aforementioned pharmaceutical compositions in unit dosage form for ease of administration and uniformity of dosage. Unit dosage form as used herein refers to physically discrete units suitable as unitary dosages, each unit containing a predetermined quantity of active ingredient calculated to produce the desired therapeutic effect in association with the required pharmaceutical carrier. Examples of such unit dosage forms are tablets (including scored or coated tablets), capsules, pills, powder packets, wafers, suppositories, injectable solutions or suspensions and the like, and segregated multiples thereof. The daily dosage of the compound according to the invention will, of course, vary with the compound employed, the mode of administration, the treatment desired and the mycobacterial disease indicated. However, in general, satisfactory results will be obtained when the compound according to the invention is administered at a daily dosage not exceeding 1 gram, e.g. in the range from 10 to 50 mg/kg body weight.

Given the fact that the compounds of formula (Ia) or Formula (Ib) are active against bacterial infections, the present compounds may be combined with other antibacterial agents in order to effectively combat bacterial infections.

Therefore, the present invention also relates to a combination of (a) a compound according to the invention, and (b) one or more other antibacterial agents.

The present invention also relates to a combination of (a) a compound according to the invention, and (b) one or more other antibacterial agents, for use as a medicine.

The present invention also relates to the use of a combination or pharmaceutical composition as defined directly above for the treatment of a bacterial infection.

A pharmaceutical composition comprising a pharmaceutically acceptable carrier and, as active ingredient, a therapeutically effective amount of (a) a compound according to the invention, and (b) one or more other antibacterial agents, is also comprised by the present invention.

The weight ratio of (a) the compound according to the invention and (b) the other antibacterial agent(s) when given as a combination may be determined by the person skilled in the art. Said ratio and the exact dosage and frequency of administration depends on the particular compound according to the invention and the other antibacterial agent(s) used, the particular condition being treated, the severity of the condition being treated, the age, weight, gender, diet, time of administration and general physical condition of the particular patient, the mode of administration as well as other medication the individual may be taking, as is well known to those skilled in the art. Furthermore, it is evident that the effective daily amount may be lowered or increased depending on the response of the treated subject and/or depending on the evaluation of the physician prescribing the compounds of the instant invention. A particular weight ratio for the present compound of the invention and another antibacterial agent may range from 1/10 to 10/1, more in particular from 1/5 to 5/1, even more in particular from 1/3 to 3/1.

The compounds according to the invention and the one or more other antibacterial agents may be combined in a single preparation or they may be formulated in separate preparations so that they can be administered simultaneously, separately or sequentially. Thus, the present invention also relates to a product containing (a) a compound according to the invention, and (b) one or more other antibacterial agents, as a combined preparation for simultaneous, separate or sequential use in the treatment of a bacterial infection.

The other antibacterial agents which may be combined with the compounds of the invention are for example antibacterial agents known in the art. The other antibacterial agents comprise antibiotics of the β-lactam group such as natural penicillins, semisynthetic penicillins, natural cephalosporins, semisynthetic cephalosporins, cephamycins, 1-oxacephems, clavulanic acids, penems, carbapenems, nocardicins, monobactams; tetracyclines, anhydrotetracyclines, anthracyclines; aminoglycosides; nucleosides such as N-nucleosides, C-nucleosides, carbocyclic nucleosides, blasticidin S; macrolides such as 12-membered ring macrolides, 14-membered ring macrolides, 16-membered ring macrolides; ansamycins; peptides such as bleomycins, gramicidins, polymyxins, bacitracins, large ring peptide antibiotics containing lactone linkages, actinomycins, amphomycin, capreomycin, distamycin, enduracidins, mikamycin, neocarzinostatin, stendomycin, viomycin, virginiamycin; cycloheximide; cycloserine; variotin; sarkomycin A; novobiocin; griseofulvin; chloramphenicol; mitomycins; fumagillin; monensins; pyrrolnitrin; fosfomycin; fusidic acid; D-(p-hydroxyphenyl)glycine; D-phenylglycine; enediynes.

Specific antibiotics which may be combined with the present compounds of the invention are for example benzylpenicillin (potassium, procaine, benzathine), phenoxymethylpenicillin (potassium), phenethicillin potassium, propicillin, carbenicillin (disodium, phenyl sodium, indanyl sodium), sulbenicillin, ticarcillin disodium, methicillin sodium, oxacillin sodium, cloxacillin sodium, dicloxacillin, flucloxacillin, ampicillin, mezlocillin, piperacillin sodium, amoxicillin, ciclacillin, hectacillin, sulbactam sodium, talampicillin hydrochloride, bacampicillin hydrochloride, pivmecillinam, cephalexin, cefaclor, cephaloglycin, cefadroxil, cephradine, cefroxadine, cephapirin sodium, cephalothin sodium, cephacetrile sodium, cefsulodin sodium, cephaloridine, cefatrizine, cefoperazone sodium, cefamandole, vefotiam hydrochloride, cefazolin sodium, ceftizoxime sodium, cefotaxime sodium, cefmenoxime hydrochloride, cefuroxime, ceftriaxone sodium, ceftazidime, cefoxitin, cefmetazole, cefotetan, latamoxef, clavulanic acid, imipenem, aztreonam, tetracycline, chlortetracycline hydrochloride, demethylchlortetracycline, oxytetracycline, methacycline, doxycycline, rolitetracycline, minocycline, daunorubicin hydrochloride, doxorubicin, aclarubicin, kanamycin sulfate, bekanamycin, tobramycin, gentamycin sulfate, dibekacin, amikacin, micronomicin, ribostamycin, neomycin sulfate, paromomycin sulfate, streptomycin sulfate, dihydrostreptomycin, destomycin A, hygromycin B, apramycin, sisomicin, netilmicin sulfate, spectinomycin hydrochloride, astromicin sulfate, validamycin, kasugamycin, polyoxin, blasticidin S, erythromycin, erythromycin estolate, oleandomycin phosphate, tracetyloleandomycin, kitasamycin, josamycin, spiramycin, tylosin, ivermectin, midecamycin, bleomycin sulfate, peplomycin sulfate, gramicidin S, polymyxin B, bacitracin, colistin sulfate, colistinmethanesulfonate sodium, enramycin, mikamycin, virginiamycin, capreomycin sulfate, viomycin, enviomycin, vancomycin, actinomycin D, neocarzinostatin, bestatin, pepstatin, monensin, lasalocid, salinomycin, amphotericin B, nystatin, natamycin, trichomycin, mithramycin, lincomycin, clindamycin, clindamycin palmitate hydrochloride, flavophospholipol, cycloserine, pecilocin, griseofulvin, chloramphenicol, chloramphenicol palmitate, mitomycin C, pyrrolnitrin, fosfomycin, fusidic acid, bicozamycin, tiamulin, siccanin.

Other Mycobacterial agents which may be combined with the compounds of the invention are for example rifampicin (=rifampin); isoniazid; pyrazinamide; amikacin; ethionamide; ethambutol; streptomycin; para-aminosalicylic acid; cycloserine; capreomycin; kanamycin; thioacetazone; PA-824; quinolones/fluoroquinolones such as for example moxifloxacin, gatifloxacin, ofloxacin, ciprofloxacin, sparfloxacin; macrolides such as for example clarithromycin, clofazimine, amoxycillin with clavulanic acid; rifamycins; rifabutin; rifapentine; the compounds disclosed in WO2004/011436.

GENERAL PREPARATION

The compounds according to the invention can generally be prepared by a succession of steps, each of which is known to the skilled person.

For instance, compounds of formula (I) may be prepared by:
(i) reaction of a compound of formula (II),

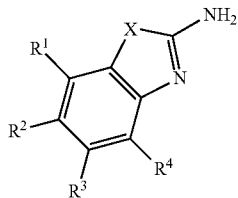
(II)

wherein X, $R^1$, $R^2$, $R^3$ and $R^4$ are as hereinbefore defined, with a compound of formula (III),

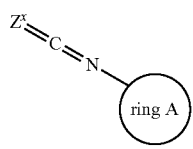
(III)

wherein ring A and $Z^x$ are as hereinbefore defined, under standard reaction conditions known to those skilled in the art, for instance in the presence of a base (e.g. an organic base, such as an amine base e.g. $Et_3N$) and a suitable solvent (e.g. a polar aprotic solvent, such as THF);
(ii) reaction of a compound of formula (IV),

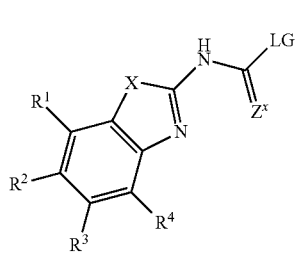
(IV)

wherein LG represents a suitable leaving group, such as an imidazolyl group or a suitable chloroformate group (e.g. 4-nitrophenylchloroformate), and $R^1$, $R^2$, $R^3$, $R^4$, X and $Z^x$ are as hereinbefore defined, with a compound of formula (V),

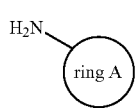
(V)

wherein ring A is as hereinbefore defined, under standard reaction conditions, for example nucleophilic substitution reaction conditions, which may be performed in the presence of a suitable solvent (such as dichloromethane).

Compounds of formula (IV) in which LG represents imidazolyl may be prepared by reaction of a compound of formula (II) as hereinbefore defined, with a compound of formula (VI),

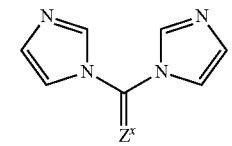
(VI)

or the like, wherein $Z^x$ is as hereinbefore defined.
Compounds of formula (V) may be prepared by:
(i) reductive amination of a compound of formula (VII),

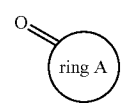
(VII)

wherein ring A is as hereinbefore defined, under standard reductive amination conditions in the presence of ammonia, or a form thereof, and a source of hydrogen (e.g. $H_2$ gas). Reagents that may be employed to form compound of formula (V) from a compound of formula (VII) include several known in the prior art, such as ammonium hydroxide, ammonia solution in methanol, ammonium formate, benzylamine or the like, and preparation may be via the oxyme (*J. Org. Chem,* 76(11), 4432-4433) or via $N_3$;
(ii) for compounds in which ring A represents ring (i), i.e. in which $R^x$ is present, but represents an optionally substituted alkyl group (as hereinbefore defined), by conversion of a compound of formula (VIII),

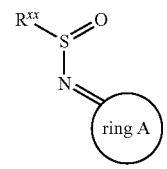
(VIII)

wherein $R^{xx}$ represents $C_{1-6}$ alkyl (e.g. tert-butyl) and ring A is as hereinbefore defined, with a compound of formula (IX),

$R^x$-$T^x$ (IX)

wherein $T^x$ represents e.g. an organometal such as lithium (which may be generated in situ) or the like and $R^x$ is as hereinbefore defined, followed by quench with a proton source (e.g. water) and removal of the —S(O)—$R^{xx}$ moiety, for instance by hydrolysis (e.g. aqueous acid hydrolysis) or the like.

Compounds of formula (VIII) may be prepared by reaction of a compound of formula (VII) as hereinbefore defined, with a compound of formula (X),

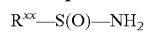
$R^{xx}$—S(O)—$NH_2$ (X)

wherein $R^{xx}$ is as hereinbefore defined, with a compound of formula (V) as hereinbefore defined, for example under condensation reaction conditions known to those skilled in the art.

Functional groups may also be converted one to another, for example, the —C(O)R$^{y4}$ group may be reduced to a —CH$_2$—R$^{y5}$ group (where the R$^{y4}$ and R$^{y5}$ moieties are the same, preferably the same alkyl group).

EXPERIMENTAL PART

Preparation of Compound 1

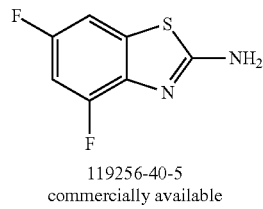
119256-40-5
commercially available

+

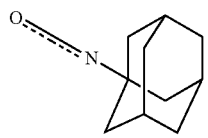

$\xrightarrow{\text{Et}_3\text{N, THF, 60}° \text{ C. o.n.}}$

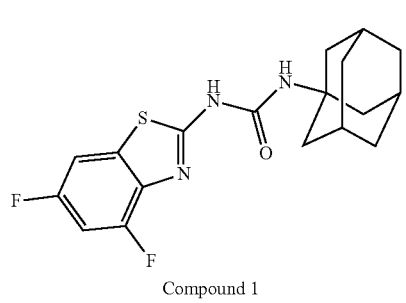
Compound 1

A solution of 2-Amino-4,6-difluoro-1,3-benzothiazole (119256-40-5, 0.22 g, 1.18 mmol), 1-Adamantyl isocyanate (0.42 g, 2.36 mmol) and triethylamine (0.27 mL, 1.97 mmol) in THF (4 mL) was stirred and heated overnight at 60° C. The solution was cooled down to room temperature. Water and DCM were added. The organic layer was separated, dried over MgSO$_4$, filtered and evaporated. The residue was purified by preparative LC on (dry loading 25 g+5 g 15-40 μm merck). Mobile phase (Gradient from 90% HEPTANE, 10% AcOEt to 70% HEPTANE, 30% AcOEt). Pure fractions were collected and evaporated to give a white powder, 0.125 g. This compound was then purified by achiral SFC on (DIETHYLAMINOPROPYL 5 μm 150×21.2 mm). Mobile phase (75% CO2, 25% MeOH). Pure fractions were collected and evaporated to a white powder, 0.09 g.

The residue was crystallized from DIPE, filtered off and dried under vacuum at 60° C. to give Compound 1 as a white powder, 0.084 g, 20%, m.p.>260° C.

$^1$H NMR (400 MHz, DMSO-d$_6$) δ 10.67 (br. s., 1H), 7.70 (dd, J=1.5, 8.1 Hz, 1H), 7.22-7.31 (m, 1H), 7.05 (d, J=8.1 Hz, 1H), 3.84 (d, J=8.1 Hz, 1H), 1.57-1.90 (m, 14H)

Preparation of Compound 2

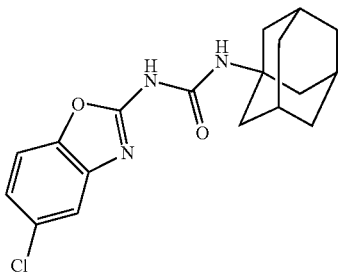
Compound 2

Compound 2 was prepared in the same way as Compound 1 from 2-amino-5-chlorobenzoxazole (61-80-3, 0.2 g, 1.19 mmol) affording the expected Compound 2, 0.161 g, 39%, m.p.>250° C.

$^1$H NMR (500 MHz, DMSO-d$_6$) δ 10.98 (br. s., 1H), 8.16 (br. s., 1H), 7.48-7.61 (m, 2H), 7.23 (dd, J=2.1, 8.7 Hz, 1H), 1.95-2.15 (m, 9H), 1.66 (br. s., 6H)

Preparation of Compound 3

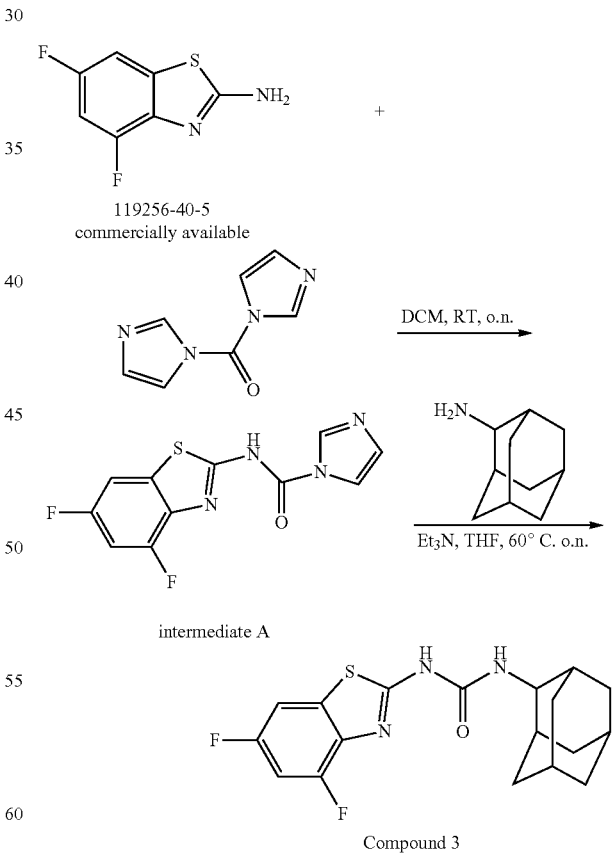

A solution of 2-Amino-4,6-difluoro-1,3-benzothiazole (3 g, 16.11 mmol) and 1,1'-carbonyldiimidazole (2.87 g, 17.72 mmol) in dichloromethane (60 mL) was stirred overnight at room temperature. The precipitate was filtered off, washed with EtOH and dried under vacuum at 60° C. affording intermediate A as a white powder, 2.49 g, 55%, used as such for next step.

A solution of intermediate A (1.99 g, 7.1 mmol), 2-Aminoadamantane hydrochloride (1.47 g, 7.81 mmol) and triethylamine (1.57 mL, 11.36 mmol) in THF (20 mL) was stirred at 60° C. overnight. The solution was cooled down to room temperature. Water and DCM were added. The organic layer was separated, dried over MgSO$_4$, filtered off and evaporated. The residue was purified by preparative LC (Stationary phase: irregular SiOH 15-40 μm 300 g MERCK), Mobile phase: 80% HEPTANE, 20% AcOEt). Pure fractions were collected and the solvent was evaporated to give a white powder, 0.33 g. The compound was crystallized from DIPE, filtered off and dried under vacuum at 60° C. affording Compound 3 as a white powder, 0.271 g, 10%, m.p.=272° C.

$^1$H NMR (500 MHz, DMSO-d$_6$) δ 10.56 (br. s., 1H), 7.68 (dd, J=1.6, 8.2 Hz, 1H), 7.21-7.33 (m, 1H), 6.47 (s, 1H), 2.05 (br. s., 3H), 1.95 (br. s., 6H), 1.64 (br. s., 6H)

Preparation of Compound 4

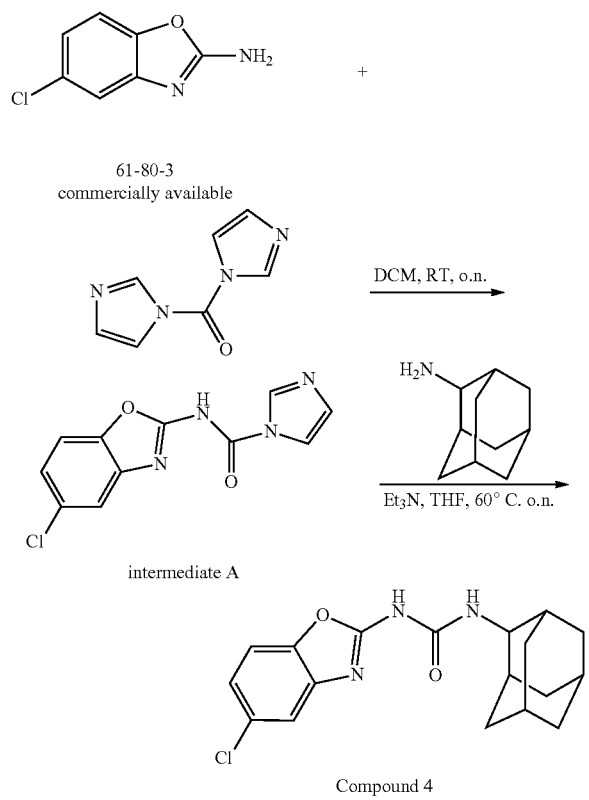

Compound 4

A solution of 2-amino-5-chlorobenzoxazole (61-80-3, 0.3 g, 1.78 mmol) and 1,1'-carbonyldiimidazole (0.32 g, 1.96 mmol) in dichloromethane (6 mL) was stirred overnight at room temperature. The precipitate was filtered off, washed with EtOH and dried under vacuum at 60° C. affording intermediate A as a white powder, 0.19 g, 40%, used as such for next step.

A solution of intermediate A (0.19 g, 0.72 mmol), 2-Aminoadamantane hydrochloride (0.15 g, 0.79 mmol) and triethylamine (0.16 mL, 1.15 mmol) in THF (4 mL) was stirred at 60° C. overnight. The solution was cooled down to room temperature. Water and DCM were added. The organic layer was separated, dried over MgSO$_4$, filtered off and evaporated. Purification was carried out by flash chromatography over silica gel (40 g, 15-40 μm, Heptane/EtOAc from 90/10 to 70/30). Pure fractions were collected and the solvent was removed. The residue was crystallized from DIPE, filtered off and dried under vacuum at 60° C. affording Compound 4 as a white powder, 0.081 g, 33%, m.p.>250° C.

$^1$H NMR (500 MHz, DMSO-d$_6$) δ 11.24 (br. s., 1H), 8.81 (d, J=7.6 Hz, 1H), 7.52-7.63 (m, 2H), 7.25 (dd, J=2.1, 8.7 Hz, 1H), 3.91 (d, J=7.6 Hz, 1H), 1.58-1.99 (m, 14H)

Preparation of Compound 5

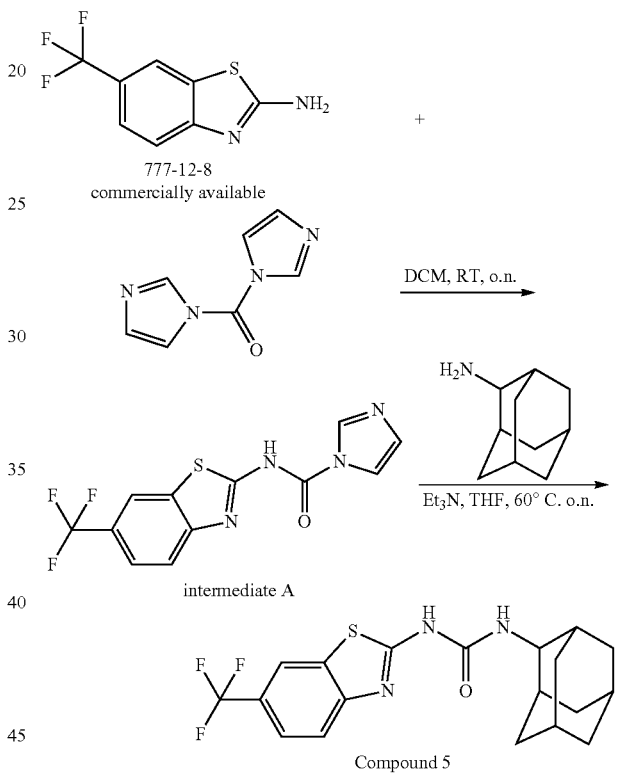

Compound 5

A solution of 2-Amino-6-(trifluoromethyl)-benzothiazole (777-12-8, 0.3 g, 1.39 mmol) and 1,1'-carbonyldiimidazole (0.25 g, 1.53 mmol) in dichloromethane (6 mL) was stirred overnight at room temperature. The precipitate was filtered off, washed with EtOH and dried under vacuum at 60° C. affording intermediate A as a white powder, 0.231 g, 53%, used as such for next step.

A solution of intermediate A (0.231 g, 0.74 mmol), 2-Aminoadamantane hydrochloride (0.15 g, 0.81 mmol) and triethylamine (0.16 mL, 1.18 mmol) in THF (8 mL) was stirred at 60° C. overnight. The solution was cooled down to room temperature. Water and DCM were added. The organic layer was separated, dried over MgSO$_4$, filtered off and evaporated. Purification was carried out by flash chromatography over silica gel (40 g, 15-40 μm, Heptane/EtOAc from 80/20 to 60/40). Pure fractions were collected and the solvent was removed. The residue was crystallized from DIPE, filtered off and dried under vacuum at 60° C. affording Compound 5 as a white powder, 0.141 g, 48%, m.p.>250° C.

$^1$H NMR (500 MHz, DMSO-d$_6$) δ 10.69 (br. s., 1H), 8.39 (s, 1H), 7.77 (d, J=8.5 Hz, 1H), 7.66 (dd, J=1.6, 8.5 Hz, 1H), 7.12 (d, J=7.9 Hz, 1H), 3.84 (d, J=7.9 Hz, 1H), 1.69-1.91 (m, 13H), 1.55-1.64 (m, 1H)

Preparation of Compound 6

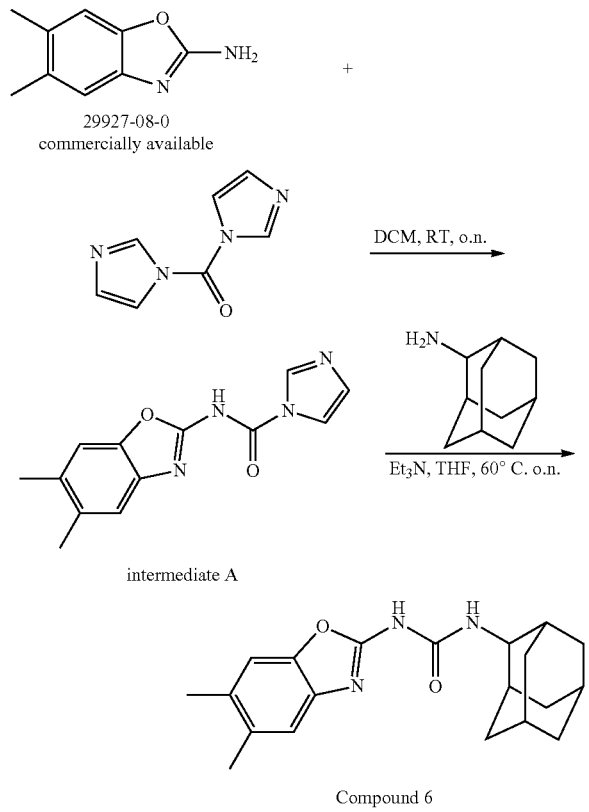

Compound 6

Preparation of Compound 7

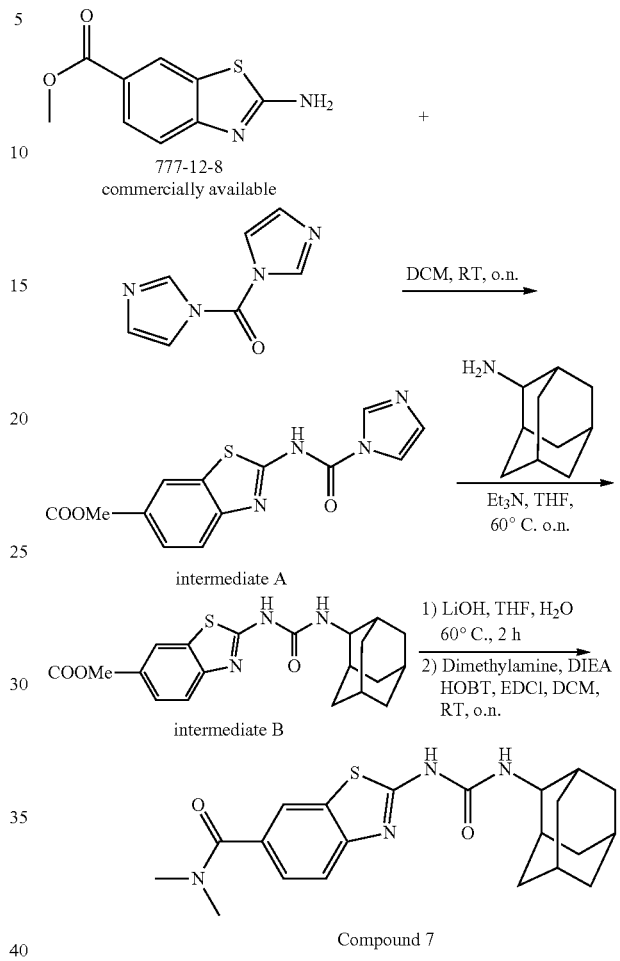

Compound 7

A solution of 2-Amino-5,6-dimethyl-benzothiazole (29927-08-0, 0.25 g, 1.39 mmol) and 1,1'-carbonyldiimidazole (0.25 g, 1.53 mmol) in dichloromethane (6 mL) was stirred overnight at room temperature. The precipitate was filtered off, washed with EtOH and dried under vacuum at 60° C. affording intermediate A as a white powder, 0.351 g, 93%, used as such for next step.

A solution of intermediate A (0.351 g, 1.29 mmol), 2-Aminoadamantane hydrochloride (0.27 g, 1.42 mmol) and triethylamine (0.29 mL, 2.06 mmol) in THF (8 mL) was stirred at 60° C. overnight. The solution was cooled down to room temperature. Water and DCM were added. The organic layer was separated, dried over MgSO$_4$, filtered off and evaporated. Purification was carried out by flash chromatography over silica gel (40 g, 15-40 μm, Heptane/EtOAc from 90/10 to 70/30). Pure fractions were collected and the solvent was removed. The residue was crystallized from DIPE, filtered off and dried under vacuum at 60° C. affording Compound 6 as a white powder, 0.038 g, 8%, m.p.>260° C.

$^1$H NMR (500 MHz, DMSO-d$_6$) δ 10.36 (br. s., 1H), 7.60 (s, 1H), 7.40 (s, 1H), 7.17 (br. s., 1H), 3.82 (d, J=7.2 Hz, 1H), 2.28 (d, J=4.7 Hz, 6H), 1.54-1.89 (m, 14H)

A solution of 2-Amino-benzothiazole-6-carboxylic acid methyl ester (0.3 g, 1.46 mmol) and 1,1'-carbonyldiimidazole (0.26 g, 1.6 mmol) in dichloromethane (6 mL) was stirred overnight at room temperature. The precipitate was filtered off, washed with EtOH and dried under vacuum at 60° C. affording intermediate A as a white powder, 0.426 g, 97%, used as such for next step.

A solution of intermediate A (0.426 g, 1.41 mmol), 2-Aminoadamantane hydrochloride (0.29 g, 1.55 mmol) and triethylamine (0.31 mL, 2.25 mmol) in THF (8 mL) was stirred at 60° C. overnight. The solution was cooled down to room temperature. Water and CH$_2$Cl$_2$ were added. The organic layer was separated, dried over MgSO$_4$, filtered off and evaporated. The residue was purified by achiral SFC (Stationary phase: DIETHYLAMINOPROPYL 5 μm 150× 21.2 mm), Mobile phase: 85% CO2, 15% MeOH). Pure fractions were collected and the solvent was evaporated to give intermediate B as a white powder, 0.23 g, 42%.

Lithium hydroxide monohydrate (0.22 g, 2.88 mmol) was added portion wise to a solution of intermediate B (0.222 g, 0.58 mmol) in THF (3 mL) and water (0.3 mL). The solution was stirred and heated at 60° C. for 2 hours. THF was evaporated and the mixture was acidified with HCl 3N. AcOEt was added, and the organic layer was separated, dried over MgSO$_4$, filtered and evaporated to give 0.085 g, 40%.

A solution of this intermediate (0.085 g, 0.23 mmol), Dimethylamine hydrochloride (0.028 g, 0.34 mmol), 1-hydroxybenzotriazole (0.037 g, 0.27 mmol), 1-(3-Dimethylaminopropoyl)-3-ethylcarbodiimide hydrochloride (0.053 g, 0.27 mmol) and N,N-diisopropylethylamine (0.082 g, 0.46 mmol) in $CH_2Cl_2$ (2 mL) was stirred overnight at room temperature. Water and $CH_2Cl_2$ were added. The organic layer was extracted, washed twice with brine, dried over $MgSO_4$, filtered and evaporated.

Purification was carried out by flash chromatography over silicagel (15-40 μm, 24 g, CMA from 100/0/0 to 97/3/0.1). Pure fractions were collected and the solvent was evaporated to give Compound 7 as a white powder, 0.036 g, 39%, m.p.=224° C.

$^1$H NMR (500 MHz, DMSO-$d_6$) δ 10.56 (br. s., 1H), 7.97 (s, 1H), 7.62 (d, J=8.2 Hz, 1H), 7.39 (dd, J=1.4, 8.2 Hz, 1H), 7.14 (d, J=5.7 Hz, 1H), 3.84 (d, J=5.7 Hz, 1H), 2.97 (br. s., 6H), 1.54-1.91 (m, 14H)

Analytical Methods

LCMS

The mass of some compounds was recorded with LCMS (liquid chromatography mass spectrometry). The methods used are described below.

General Procedure A

The HPLC measurement was performed using an Alliance HT 2795 (Waters) system comprising a quaternary pump with degasser, an autosampler, a diode-array detector (DAD) and a column as specified in the respective methods below, the column is hold at a temperature of 30° C. Flow from the column was split to a MS spectrometer. The MS detector was configured with an electrospray ionization source. The capillary needle voltage was 3.15 kV and the source temperature was maintained at 110° C. on the ZQ™ (simple quadrupole Zspray™ mass spectrometer from Waters). Nitrogen was used as the nebulizer gas. Data acquisition was performed with a Waters-Micromass MassLynx-Openlynx data system.

General Procedure B

The LC measurement was performed using an Acquity UPLC (Waters) system comprising a binary pump, a sample organizer, a column heater (set at 55° C.), a diode-array detector (DAD) and a column as specified in the respective methods below. Flow from the column was split to a MS spectrometer. The MS detector was configured with an electrospray ionization source. Mass spectra were acquired by scanning from 100 to 1000 in 0.18 seconds using a dwell time of 0.02 seconds. The capillary needle voltage was 3.5 kV and the source temperature was maintained at 140° C. Nitrogen was used as the nebulizer gas. Data acquisition was performed with a Waters-Micromass MassLynx-Openlynx data system.

General procedure C

The HPLC measurement was performed using an Agilent 1100 series liquid chromatography system comprising a binary pump with degasser, an autosampler, a column oven, a UV detector and a column as specified in the respective methods below. Flow from the column was split to a MS spectrometer. The MS detector was configured with an electrospray ionization source. The capillary voltage was 3 kV, the quadrupole temperature was maintained at 100° C. and the desolvation temperature was 300° C. Nitrogen was used as the nebulizer gas. Data acquisition was performed with an Agilent Chemstation data system.

General Procedure D

The LC measurement was performed using a UPLC (Ultra Performance Liquid Chromatography) Acquity (Waters) system comprising a binary pump with degasser, an autosampler, a diode-array detector (DAD) and a column as specified in the respective methods below, the column is hold at a temperature of 40° C. Flow from the column was brought to a MS detector. The MS detector was configured with an electrospray ionization source. The capillary needle voltage was 3 kV and the source temperature was maintained at 130° C. on the Quattro (triple quadrupole mass spectrometer from Waters). Nitrogen was used as the nebulizer gas. Data acquisition was performed with a Waters-Micromass MassLynx-Openlynx data system.

Method 1

In addition to general procedure A: Reversed phase HPLC was carried out on a Sunfire C18 column (3.5 μm, 4.6×100 mm) with an initial flow rate of 0.8 ml/min. Two mobile phases (mobile phase A: 35% 6.5 mM ammonium acetate+30% acetonitrile+35% formic acid (2 ml/1); mobile phase B: 100% acetonitrile) were employed to run a gradient condition from 100% A (hold for 1 minute) to 100% B in 4 minutes, hold at 100% B at a flow rate of 1.2 ml/min for 4 minutes and reequilibrated with initial conditions for 3 minutes. An injection volume of 10 μl was used. Cone voltage was 20 V for positive and negative ionization mode. Mass spectra were acquired by scanning from 100 to 1000 in 0.4 seconds using an interscan delay of 0.3 seconds.

Method 2

In addition to general procedure A: Reversed phase HPLC was carried out on a Sunfire C18 column (3.5 μm, 4.6×100 mm) with an initial flow rate of 0.8 ml/min. Two mobile phases (mobile phase A: 25% 7 mM ammonium acetate+50% acetonitrile+25% formic acid (2 ml/1); mobile phase B: 100% acetonitrile) were employed to run a gradient condition from 100% A (hold for 1 minute) to 100% B in 4 minutes, hold at 100% B at a flow rate of 1.2 ml/min for 4 minutes and reequilibrated with initial conditions for 3 minutes). An injection volume of 10 μl was used. Cone voltage was 20 V for positive and negative ionization mode. Mass spectra were acquired by scanning from 100 to 1000 in 0.4 seconds using an interscan delay of 0.3 seconds.

Method 3

In addition to general procedure B: Reversed phase UPLC (Ultra Performance Liquid Chromatography) was carried out on a bridged ethylsiloxane/silica hybrid (BEH) C18 column (1.7 μm, 2.1×50 mm; Waters Acquity) with a flow rate of 0.8 ml/min. Two mobile phases (mobile phase A: 0.1% formic acid in $H_2O$/methanol 95/5; mobile phase B: methanol) were used to run a gradient condition from 95% A and 5% B to 5% A and 95% B in 1.3 minutes and hold for 0.2 minutes. An injection volume of 0.5 μl was used. Cone voltage was 10 V for positive ionization mode and 20 V for negative ionization mode.

Method 4

In addition to general procedure C: Reversed phase HPLC was carried out on a YMC-Pack ODS-AQ C18 column (4.6×50 mm) with a flow rate of 2.6 ml/min. A gradient run was used from 95% water and 5% acetonitrile to 95% acetonitrile in 7.30 minutes and was hold for 1.20 minutes. Mass spectra were acquired by scanning from 100 to 1000. Injection volume was 10 μl. Column temperature was 35° C.

Method 5

In addition to general procedure A: Reversed phase HPLC was carried out on a Sunfire C18 column (3.5 μm, 4.6×100 mm) with an initial flow rate of 0.8 ml/min. Two mobile phases (mobile phase A: 35% 6.5 mM ammonium acetate+30% acetonitrile+35% formic acid (2 ml/1); mobile phase B: 100% acetonitrile) were employed to run a gradient condition from 100% A (hold for 1 minute) to 100% B in 4 minutes, hold at 100% B at a flow rate of 1.2 ml/min for 4 minutes and reequilibrated with initial conditions for 3 minutes. An injection volume of 10 µl was used. Positive ionization mode was used with four different cone voltages (20, 40, 50, 55 V). Mass spectra were acquired by scanning from 100 to 1000 in 0.4 seconds using an interscan delay of 0.1 seconds.

Method 6

In addition to general procedure D: Reversed phase UPLC was carried out on a Waters Acquity BEH (bridged ethylsiloxane/silica hybrid) C18 column (1.7 µm, 2.1×100 mm) with a flow rate of 0.35 ml/min. Two mobile phases (mobile phase A: 95% 7 mM ammonium acetate/5% acetonitrile; mobile phase B: 100% acetonitrile) were employed to run a gradient condition from 90% A and 10% B (hold for 0.5 minutes) to 8% A and 92% B in 3.5 minutes, hold for 2 min and back to the initial conditions in 0.5 min, hold for 1.5 minutes. An injection volume of 2 µl was used. Cone voltages were 20, 30, 45, 60 V for positive ionization mode. Mass spectra were acquired by scanning from 100 to 1000 in 0.2 seconds using an interscan delay of 0.1 seconds.

Method 7

In addition to general procedure D: Reversed phase UPLC was carried out on a Thermo Hypersil Gold C18 column (1.9 µm, 2.1×100 mm) with a flow rate of 0.40 ml/min. Two mobile phases (mobile phase A: 95% 7 mM ammonium acetate/5% acetonitrile; mobile phase B: 100% acetonitrile) were employed to run a gradient condition from 72% A and 28% B (hold for 0.5 minutes) to 8% A and 92% B in 3.5 minutes, hold for 2 min and back to the initial conditions in 0.5 min, hold for 1.5 minutes. An injection volume of 2 µl was used. Cone voltages were 20, 30, 45, 60 V for positive ionization mode. Mass spectra were acquired by scanning from 100 to 1000 in 0.2 seconds using an interscan delay of 0.1 seconds.

Method 8

In addition to general procedure D: Reversed phase UPLC was carried out on a Waters Acquity BEH (bridged ethylsiloxane/silica hybrid) C18 column (1.7 µm, 2.1×100 mm) with a flow rate of 0.35 ml/min. Two mobile phases (mobile phase A: 100% 7 mM ammonium acetate; mobile phase B: 100% acetonitrile) were employed to run a gradient condition from 75% A and 25% B (hold for 0.5 minutes) to 8% A and 92% B in 3.5 minutes, hold for 2 minutes and reequilibrated with initial conditions for 2 minutes. An injection volume of 2 µl was used. Cone voltages were 20, 30, 45, 60 V for positive ionization mode. Mass spectra were acquired by scanning from 100 to 1000 in 0.2 seconds using an interscan delay of 0.1 seconds.

Method 9

In addition to general procedure D: Reversed phase UPLC was carried out on a Thermo Hypersil Gold C18 column (1.9 µm, 2.1×100 mm) with a flow rate of 0.50 ml/min. Two mobile phases (mobile phase A: 95% 7 mM ammonium acetate/5% acetonitrile; mobile phase B: 100% acetonitrile) were employed to run a gradient condition from 40% A and 60% B (hold for 0.5 minutes) to 5% A and 95% B in 3.5 minutes, hold for 2 min and back to the initial conditions in 0.5 min, hold for 1.5 minutes. An injection volume of 2 µl was used. Cone voltages were 20, 30, 45, 60 V for positive ionization mode. Mass spectra were acquired by scanning from 100 to 1000 in 0.2 seconds using an interscan delay of 0.1 seconds.

Method 10

In addition to general procedure A: Reversed phase HPLC was carried out on a Varian Pursuit Diphenyl column (5 µm, 4×100 mm) with a flow rate of 0.8 ml/min. Two mobile phases (mobile phase A: 100% 7 mM ammonium acetate; mobile phase B: 100% acetonitrile) were employed to run a gradient condition from 80% A, 20% B (hold for 0.5 minutes) to 90% B in 4.5 minutes, 90% B for 4 minutes and reequilibrated with initial conditions for 3 minutes. An injection volume of 10 µl was used. Cone voltages were 20, 40, 50, 55 V for positive ionization mode. Mass spectra were acquired by scanning from 100 to 1000 in 0.3 seconds using an interscan delay of 0.05 seconds.

When a compound is a mixture of isomers which give different peaks in the LCMS method, only the retention time of the main component is given in the LCMS table.

D. Pharmacological Examples $MIC_{90}$ Determination for Testing Compounds Against *M. tuberculosis*

Flat-bottom, sterile 96-well plastic microtiter plates were filled with 100 µl of Middlebrook (1×) 7H9 broth medium. Subsequently, an extra 100 µl medium was added to column 2. Stock solutions (200×final test concentration) of compounds were added in 2 µl volumes to a series of duplicate wells in column 2 so as to allow evaluation of their effects on bacterial growth. Serial 2-fold dilutions were made directly in the microtiter plates from column 2 to 11 using a multipipette. Pipette tips were changed after every 3 dilutions to minimize pipetting errors with high hydrophobic compounds. Untreated control samples with (column 1) and without (column 12) inoculum were included in each microtiter plate. Approximately 10000 CFU per well of *Mycobacterium tuberculosis* (strain H37RV), in a volume of 100 µl in Middlebrook (1×) 7H9 broth medium, was added to the rows A to H, except column 12. The same volume of broth medium without inoculum was added to column 12 in row A to H. The cultures were incubated at 37° C. for 7 days in a humidified atmosphere (incubator with open air valve and continuous ventilation). On day 7 the bacterial growth was checked visually.

The 90% minimal inhibitory concentration ($MIC_{90}$) was determined as the concentration with no visual bacterial growth.

Time Kill Assays

Bactericidal or bacteriostatic activity of the compounds can be determined in a time kill assay using the broth dilution method. In a time kill assay on *Mycobacterium tuberculosis* (strain H37RV), the starting inoculum of *M. tuberculosis* is $10^6$ CFU/ml in Middlebrook (1×) 7H9 broth. The antibacterial compounds are used at the concentration of 0.1 to 10 times the $MIC_{90}$. Tubes receiving no antibacterial agent constitute the culture growth control. The tubes containing the microorganism and the test compounds are incubated at 37° C. After 0, 1, 4, 7, 14 and 21 days of incubation samples are removed for determination of viable counts by serial dilution ($10^{-1}$ to $10^{-6}$) in Middlebrook 7H9 medium and plating (100 µl) on Middlebrook 7H11 agar. The plates are incubated at 37° C. for 21 days and the number of colonies are determined. Killing curves can be constructed by plotting the $\log_{10}$ CFU per ml versus time. A bactericidal effect is commonly defined as 3-$\log_{10}$ decrease in number of CFU per ml as compared to untreated inoculum. The potential carryover effect of the drugs is removed by serial dilutions and counting the colonies at highest dilution used for plating.

MIC Values

| | MIC90 (µg/ml) | | | |
|---|---|---|---|---|
| | LV12076 | | LV12086 | |
| Compound | No human serum | 10% human serum | No human serum | 20% human serum |
| Compound 1 | 0.5 | 1 | 0.25 | 1 |
| | 0.5 | 1 | 0.25 | 1 |
| Compound 3 | 0.06 | 0.25 | 0.03 | 0.25 |
| | 0.06 | 0.25 | 0.03 | 0.25 |
| Isoniazid | 0.03 | 0.03 | 0.03 | 0.03 |
| | 0.03 | 0.03 | 0.03 | 0.03 |

This experiment was done in microplates; starting from dry powder.

Kill Kinetics

| | | log CFU/ml (and days) | | | | | |
|---|---|---|---|---|---|---|---|
| strain | compound | 0 | 1 | 4 | 7 | 14 | 21 |
| H37RV | Control | 6.35 | 6.52 | 6.84 | 8.00 | 7.96 | 9.19 |
| | Compound 1 - 0.5 µg/ml | 6.35 | 5.57 | 2.00 | 2.00 | 2.00 | 2.00 |
| | Compound 1 - 5 µg/ml | 6.35 | 6.15 | 3.08 | 2.00 | 2.00 | 2.00 |
| | Compound 3 - 0.06 µg/ml | 6.35 | 5.64 | 2.60 | 2.00 | 2.00 | 2.00 |
| | Compound 3 0.6 µg/ml | 6.35 | 5.40 | 3.32 | 2.00 | 2.00 | 2.00 |
| | Isoniazid 1 µg/ml | 6.35 | 3.57 | 2.00 | 2.00 | 2.00 | 2.00 |

The invention claimed is:

1. A compound selected from the group consisting of:

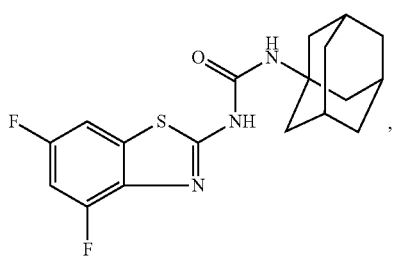

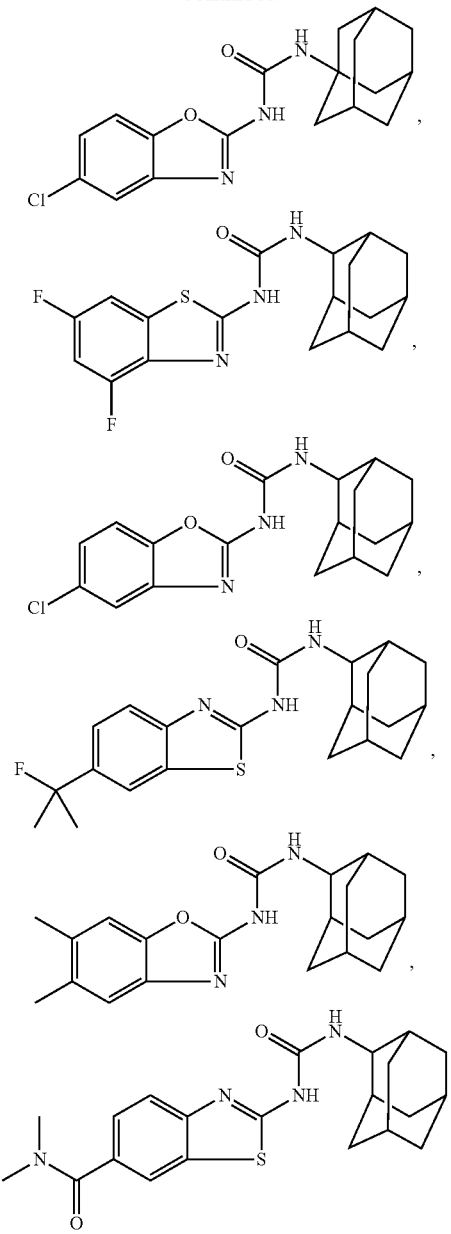

and pharmaceutically acceptable salts thereof.

2. A pharmaceutical composition comprising a compound as claimed in claim 1 and a pharmaceutically acceptable carrier.

* * * * *

UNITED STATES PATENT AND TRADEMARK OFFICE
CERTIFICATE OF CORRECTION

PATENT NO.        : 9,758,497 B2
APPLICATION NO.   : 15/231389
DATED             : September 12, 2017
INVENTOR(S)       : Jérôme Émile Georges Guillemont et al.

It is certified that error appears in the above-identified patent and that said Letters Patent is hereby corrected as shown below:

In the Claims

Column 30, Lines 25 to 34, the compound

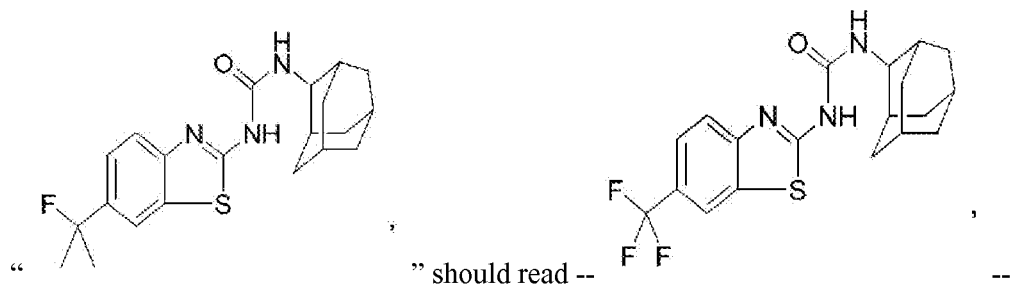

Signed and Sealed this
Twenty-sixth Day of June, 2018

Andrei Iancu
*Director of the United States Patent and Trademark Office*